June 12, 1962 G. MERRILL Plant Pat. 2,152

PEACH TREE

Filed April 17, 1961

WITNESS

Addison E. Avery

GRANT MERRILL
INVENTOR

HUEBNER & WORREL
ATTORNEYS

BY Richard M. Worrel

United States Patent Office

Plant Pat. 2,152
Patented June 12, 1962

2,152
PEACH TREE

Grant Merrill, P.O. Box 392, Red Bluff, Calif.

Filed Apr. 17, 1961, Ser. No. 103,666
1 Claim. (Cl. 47—62)

The present invention relates to a peach tree and more particularly to a new and distinct variety thereof broadly characterized by producing very highly colored yellow fleshed freestone peaches, of smooth round shape, which ripen about two weeks later than Merrill Gemfree (Plant Patent No. 1,409), but which tree blossoms relatively early.

Because of rich soil and favorable climatic environment prevailing in most of the commercial peach farming areas of California, the peach trees tend to produce rank growth and dense shade resulting in serious impairment of the coloring of the fruit. Inasmuch as most fruits rely on eye appeal for their sales, color impairment is highly undesirable. A primary object of the plant breeding procedures which have resulted in the development of this new peach variety has been to achieve a highly colored red peach which achieves its high color and firmness even under conditions of rank growth and dense shade.

Another object has been to provide a peach tree of the character described which is vigorous and healthy but of medium size so as to be susceptible to picking without excessively tall ladders and yet be of sufficient size to produce satisfactory yields when planted the usual commercial distance.

Another object has been to provide an improved yellow-fleshed, freestone peach.

Another object has been to provide a peach tree somewhat similar to the Merrill Gemfree but which is distinguished therefrom in the production of more nearly spherical fruit which has more red coloring, is more completely freestone, and ripens about two weeks later.

Further objects and advantages will become more fully apparent in the subsequent description in the specification.

In the drawing which is a water color painting:

Figure 1:
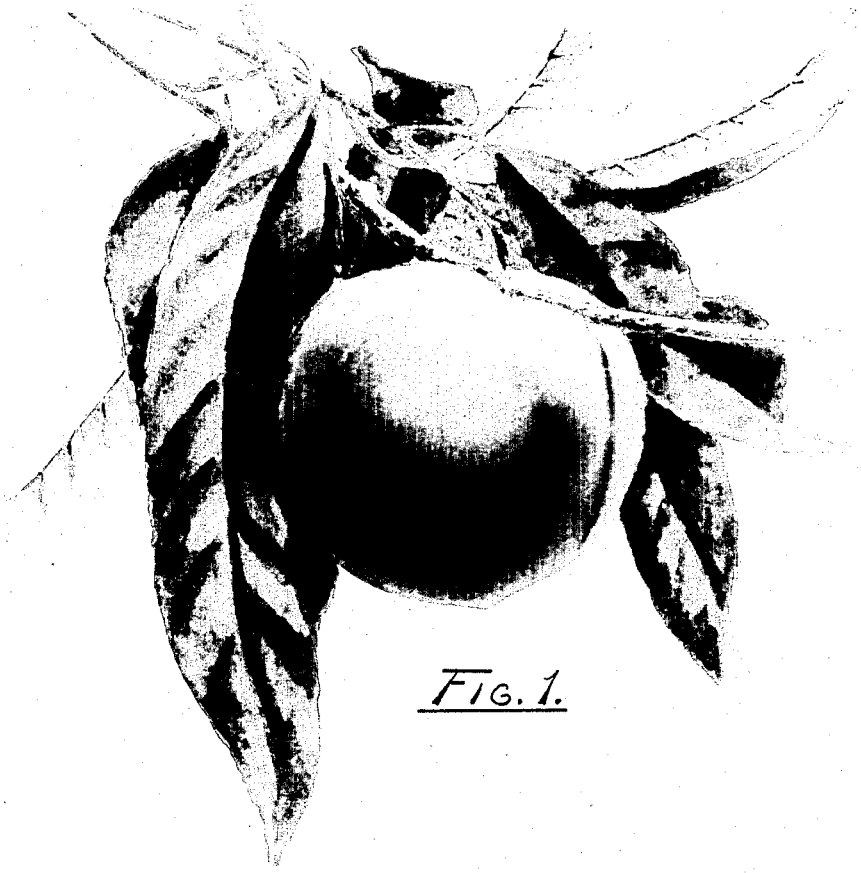
FIG. 1 shows a fruit bearing twig of the subject variety of peach tree having leaves and a mature peach thereon.
Figure 2:
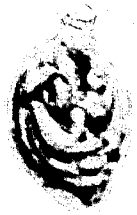
FIG. 2 shows a peach of the subject variety sectioned on its suture plane to show the flesh and stone coloration.

The most distinctive characteristics of the instant variety of peach tree are the fruit which is of very high color, of quite smooth substantially spherical shape, and the unusually early bloom for a yellow-fleshed freestone. This variety most nearly resembles the Merrill Gemfree (Plant Patent No. 1,409), one of its parents, but is an improvement thereon in that it has smoother and rounder fruit having more red on the surface of the skin, has flesh which is more free from the stone, and which ripens from ten to twenty days, averaging two weeks, later.

The new variety of peach was produced by me on my breeding farm near Red Bluff, Tehama County, California, from seeds resulting from a cross of Merrill Fortyniner (unpatented) with Merrill Gemfree (Plant Patent No. 1,409). The variety has been budded onto seedlings in my virus isolation plot, at Corning, Tehama County, California. When the buds matured they were found to possess the same characteristics as the original seedling.

Referring more specifically to the pomological characteristics of this new and distinct variety of peach tree, the following have been observed under the ecological conditions prevailing at my farm at Red Bluff, Tehama County, California, and at my virus free isolation plot at Corning, Tehama County, California. All major color plate identifications are by reference to Maerz and Paul Dictionary of Color.

*Tree*

Size: Medium small, medium upright, medium dense, vase formed by pruning, very productive, very regular bearer.

Trunk: Medium stocky, medium shaggy, grey-brown in color. Lenticels—numerous, medium small in size.

Leaves (selected from midportion of vigorous unbranched terminal shoot 18" to 24" long):

*Length.*—6" to 8".

*Width.*—Mostly about 1½".

*Form.*—Large size, lanceolate, tip acuminate, medium thin.

*Color.*—Upper surface dark green (22–L–7), under surface light green (21–K–6), with heavy under midrib, light green (19–J–1).

*Class* (Meader and Blake Proceedings: Am. Soc. Hor. Sc., vol. 37, page 206).—Class 1. Width-length ratio—.20 to .23. Apex angle (1" from tip)—28° to 30°. Base angle (½" from petiole).—79° to 80°.

*Margin.*—Finely serate.

*Petiole.*—Medium long, medium slender.

*Stipules.*—On early growth, falling off early.

*Glands.*—Reniform, usually two to three, mostly opposite, some alternate.

Flower buds: Medium size, medium short, plump, free, pubescent.

Flowers: Early bloom, about with July Elberta (Plant Patent No. 15), small, pink.

*Anthers.*—Yellow-orange.

*Pollen.*—Abundant.

*Fruit*

Maturity when described, firm ripe, approximately July 15.

Size: Uniform.

*Axial diameter.*—2⅜" to 2⅝".

*Transverse in suture plane.*—2½" to 2¾".

*At right angles to suture plane.*—2½" to 2$^{11}/_{16}$".

Form: Uniform, smooth, symmetrical, globose.

*Suture.*—Distinct, very shallow line extends from base but discontinues at apex, with slight marked depression beyond pistil point.

*Lips.*—Inconspicious.

*Cavity.*—Rounded, abrupt, slightly elongated in suture plane; depth, ⅜" to ½"; breadth, ½" to ¾"; markings yellow to mostly dark red.

*Base.*—Cuneate.

*Apex.*—Short, depressed, pistil point apical.

*Stem.*—Length, $^{3}/_{16}$" to ¼"; diameter, ⅛" to $^{3}/_{16}$". Adherence to stone—none.

Skin: Medium thick, medium tender, tenacious to flesh.

*Tendency to crack.*—None.

*Color.*—Under color, especially around stem end, dull orange (11–L–7), cheek color—dark red (5–L–6) to very dark red usually on apical end (55–L–12).

*Down.*—Scant, rolls up when rubbed.

Flesh:

*Color.*—From golden yellow (9–L–4) toward the apical end to orange yellow (9–I–7) at the cheek, and toward the base bright orange-red (3–K–10).

*Amygdalin.*—Moderate.

*Juice.*—Abundant.

*Texture.*—Very firm and meaty when shipping ripe, softening into a meaty to melting flesh when soft ripe.

*Fibers.*—Few.
*Ripens.*—Evenly to slightly sooner at the apical end.
*Flavor.*—Delicate, vinous.
*Aroma.*—Distinct.
*Eating quality.*—Good.

Stone: Free.
*Fibers.*—Short.
*Size.*—Medium.
*Form.*—Oval with distinct apical tip.
*Base.*—Oblique.
*Hilum.*—Oblong.
*Apex.*—Acuminate.
*Sides.*—Slightly unequal.
*Surface.*—Irregularly furrowed and ridged throughout, but more deeply near the base. Ridges jagged. Pitted slightly throughout, pits elongated.
*Ventral edge.*—Thick, without wing.
*Dorsal edge.*—Narrow, grooved throughout.
*Ridges.*—Partly interrupted.
*Color of stone.*—When first removed from fruit, dull tan (4–K–7) to light tan (3–A–12).

Use: Market, local, dessert, culinary, long distance shipment.

Keeping quality: Good.

Shipping quality: Good.

It is to be understood that normal variations in the described characteristics of the new variety peach tree result from environmental changes, such as in climate and soil conditions, and from changes in cultural practices, such as in pruning, thinning, fertilizing, spraying, irrigating and the like. The description is that of the variety produced under the ecological conditions prevailing at my farm at Red Bluff, Tehama County, California, and the characteristics are found to hold true in asexual reproduction of the variety.

Having described and illustrated my new variety of peach tree, what I claim as new and desire to secure by Letters Patent is:

A new and distinct variety of peach tree, substantially as illustrated and described, characterized by its relatively early blooming period and by its yellow-fleshed freestone fruit of high color and substantially spherical smooth shape and which most nearly resembles the Merrill Gemfree (Plant Patent No. 1,409) of known peach varieties but is distinguished therefrom in its redder fruit of more nearly spherical form which is somewhat more free of its stones and ripens about two weeks later.

No references cited.